(12) United States Patent
Monti

(10) Patent No.: US 8,511,518 B2
(45) Date of Patent: Aug. 20, 2013

(54) VOLUMETRIC DOSER FOR BATCHING LIQUID OR PASTY PHARMACEUTICAL SUBSTANCES

(75) Inventor: Giuseppe Monti, Pianoro (IT)

(73) Assignee: Marchesini Group S.p.A., Pianoro (Bologna) (IT)

( * ) Notice: Subject to any disclaimer, the term of this patent is extended or adjusted under 35 U.S.C. 154(b) by 182 days.

(21) Appl. No.: 13/156,838

(22) Filed: Jun. 9, 2011

(65) Prior Publication Data

US 2011/0303704 A1 Dec. 15, 2011

(30) Foreign Application Priority Data

Jun. 14, 2010 (IT) .............................. BO2010A0374

(51) Int. Cl.
*G01F 11/00* (2006.01)
(52) U.S. Cl.
USPC ....................................................... 222/386
(58) Field of Classification Search
USPC .................. 222/326, 327, 391, 386
See application file for complete search history.

(56) References Cited

U.S. PATENT DOCUMENTS

| | | | | |
|---|---|---|---|---|
| 2,505,839 A | * | 5/1950 | Scovell | .......... 222/262 |
| 5,779,105 A | | 7/1998 | Brown et al. | |
| 3,029,847 A1 | | 1/2012 | Baudhuin et al. | |
| 2007/0245893 A1 | * | 10/2007 | Chen | ............................... 92/247 |
| 2010/0147895 A1 | * | 6/2010 | Helmenstein | ................. 222/326 |

FOREIGN PATENT DOCUMENTS

| | | |
|---|---|---|
| DE | 3129348 A | 2/1983 |
| EP | 0707146 A | 4/1996 |
| EP | 1849490 A | 10/2007 |
| WO | WO2009/023463 A | 2/2009 |

OTHER PUBLICATIONS

European Search Report for EP 2 395 330 A1,Completed Aug. 4, 2011, 2 pages.

\* cited by examiner

*Primary Examiner* — Paul R Durand
*Assistant Examiner* — Donnell Long
(74) *Attorney, Agent, or Firm* — William J. Sapone; Ware Fressola Maguire & Barber LLP

(57) ABSTRACT

A volumetric doser (10) for batching liquid or pasty pharmaceutical substances is disclosed which comprises: a cylinder (1); a piston (2), mobile along internal walls (49) of the cylinder (1) for displacing liquid or pasty pharmaceutical substances; a stem (3) exiting from the cylinder (1) for moving the piston (2); and a coupling member (9) to which the stem (3) is fixable. The coupling member (9) has a substantially U-shaped form and comprises: a base (11) and two facing lateral walls (12, 13) which originate from the base (11). The piston (2) and the coupling member (9) are reciprocally conformed such that the coupling member (9) can embrace a part (17) of the piston (2) and can perform limited oscillations with respect to the piston (2) axis.

7 Claims, 3 Drawing Sheets

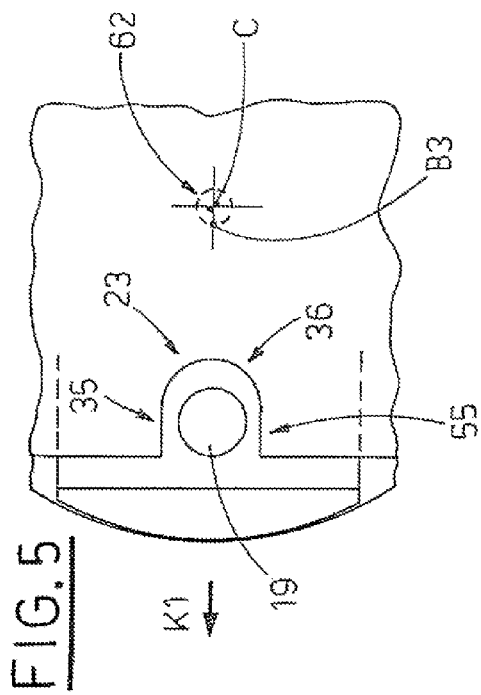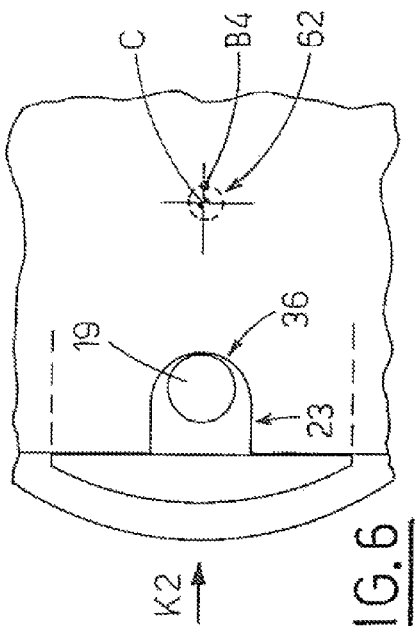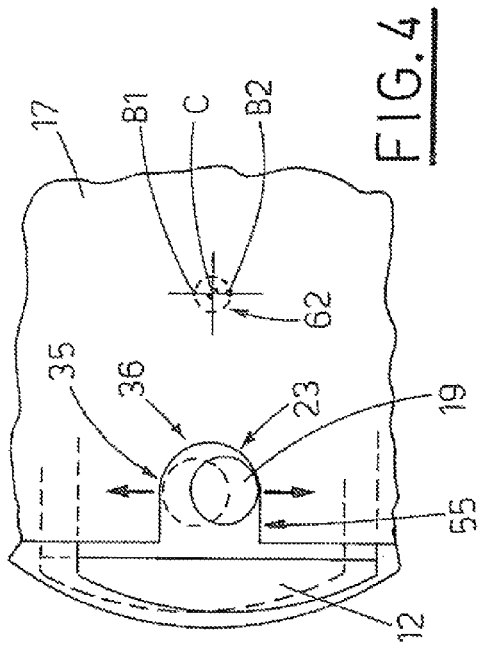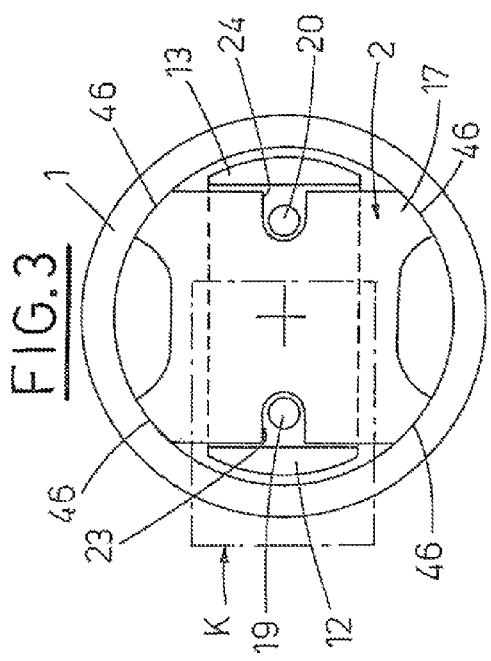

VOLUMETRIC DOSER FOR BATCHING LIQUID OR PASTY PHARMACEUTICAL SUBSTANCES

FIELD OF THE INVENTION

The present invention relates to a volumetric doser for batching liquid or pasty pharmaceutical substances, in particular usable in the pharmaceutical sector.

DESCRIPTION OF THE PRIOR ART

A known-type volumetric doser comprises: a cylinder; a piston, mobile along internal walls 49 of the cylinder 1 for displacing liquid or pasty pharmaceutical substances; a stem, rigidly fixed to the piston and exiting from the cylinder; a first cap, sealingly fixed to a first end of the cylinder and provided with a hole for entry and expulsion of liquid or pasty substances into/from the cylinder; a second cap sealingly fixed to a second end of the cylinder, opposite the first end, and provided with a through-hole for sliding of the stem; and seals arranged in the through-hole of the second cap.

A doser as described above can be connected, for example, to a three-way valve for communicating with a tank of liquid or pasty substances and to a nozzle for injecting these substances internally of corresponding containers. From the tank, the liquid or pasty substance is destined to be supplied, via the above-mentioned valves, internally of the chamber defined by the doser (identifiable by the cylinder, the piston and the first cap); then a batched quantity of liquid or pasty substances is subsequently dispensed from the nozzle and thence to a corresponding container by action of the stem-piston assembly of the batcher.

In pharmaceutical applications a question of primary importance is that the liquid or pasty substances are not contaminated by extraneous particles during their journey towards the container.

For this reason the cylinder and the piston, which are subject to mutual relative motion and delimit the chamber of the volumetric doser in which the liquid or pasty substances are temporarily received, can be made of a ceramic material; the stem, which instead does not enter into contact with the liquid or pasty substances, is usually made of stainless steel, which is a cheaper material than ceramic.

The piston and stem are rigidly fixed to one another in a known way: for example, the piston bears a plug and the stem a blind axial hole for receiving the plug via an interfering coupling; an external annular element is applied to the external surface of the stem, in proximity of the end which affords the blind hole, such as to lock the stem, thus determining the rigid connection between the stem and the piston.

The stem and the piston are thus mechanically coupled by interference and a subsequent locking of the annular element; the mutual coupling portions of the stem and the piston are thus in strict contact, pressing one against the other. Note that the stem and the piston have a different coefficient of heat dilation, as the first is made of stainless steel and the second is made of ceramic; this determines a considerable stress at the mutual coupling portions during the sterilization of the volumetric doser.

These stresses, with the repeating of the sterilization operations, can lead to breakage of the rigid connection between the stem and the piston.

A further drawback of volumetric dosers of known type is that the axis of the actuator moving the stem is not concentric to the axis of the stem; a force results which acts on the stem comprising also a transversal component with respect to the relative axis, such as to stress the rigid connection between the stem and piston. This type of stress can also lead, with the use of the volumetric doser, to the breakage of the rigid connection between the stem and the piston.

SUMMARY OF THE INVENTION

In the light of the above, an aim of the present invention consists in obviating the above-mentioned drawbacks.

The above aim is attained with a volumetric doser for batching liquid or pasty pharmaceutical substances, comprising: a cylinder; a piston, mobile along internal walls of the cylinder for displacing liquid or pasty pharmaceutical substances; a stem exiting from the cylinder for moving the piston; characterized in that: the volumetric doser is provided with a coupling member to which the stem is fixable, the coupling member having a substantially U-shaped form and comprising: a base and two facing lateral walls which originate from the base; and in that the piston and the coupling member are reciprocally conformed such that the coupling member can embrace a part of the piston and can perform limited oscillations with respect to the piston axis.

The unit formed by the coupling member and the stem, when the stem is fixed to the coupling member, can advantageously be orientated such that the axis thereof is concentric with the axis of the actuator connected to the free end of the stem, even if these axes are not concentric with the piston axis. This is enabled by the fact that the coupling member can oscillate with respect to the piston axis. It results that the force acting on the stem via the actuator is always directly only along the axis of the stem and thus does not cause transversal stresses at the coupling between the piston and the coupling member and between the coupling member and the stem.

Thanks to the possibility of the coupling member to oscillate with respect to the piston axis, the effects consequent to the heat dilation should the piston and the coupling member be realized in different materials (for example the former of ceramic and the latter of stainless steel) are also compensated for.

In this case too, then, the different coefficients of heat dilation would not produce undesired stresses in the coupling between the piston and the coupling member.

BRIEF DESCRIPTION OF THE DRAWINGS

Specific embodiments of the invention, and advantageous technical-functional characteristics thereof, only in part derivable from the above description, will now be described in the following of the present description, in accordance with what is set out in the claims and with the aid of the accompanying figures of the drawings, in which:

FIG. 3 is the view of section III-Ill of FIG. 1;

FIGS. 4, 5, 6 are enlarged-scale views of the detail K of FIG. 3, showing different positions taken on by the coupling member with respect to the piston.

DESCRIPTION OF THE PREFERRED EMBODIMENTS

Figure 1:
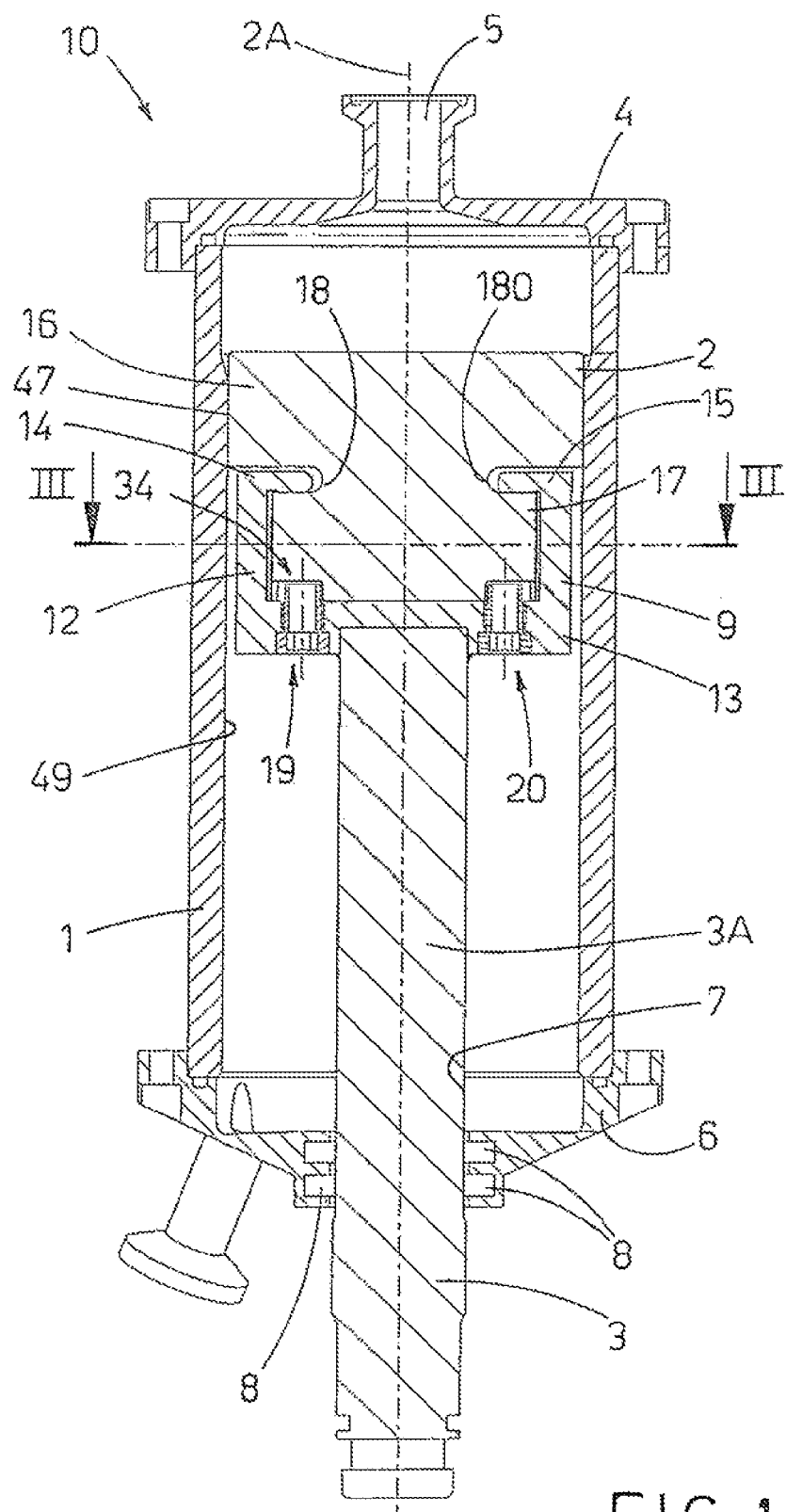
FIG. 1 is a view in axial section of a volumetric doser of the present invention.

With reference to the accompanying figures of the drawings, reference number 10 denotes the volumetric doser that is the object of the present invention, which is suitable for batching liquid or pasty pharmaceutical substances: a cylinder 1; a piston 2, mobile along internal walls 49 of the cylinder 1 for displacing liquid or pasty pharmaceutical substances (not illustrated); a stem 3 exiting from the cylinder 1 for moving the piston 2; a first cap 4 sealingly fixed to a first end of the cylinder 1 and provided with a hole 5 for introduction and expulsion of liquid or pasty substances into/from the cylinder 1; a second cap 6 sealingly fixed to a second end of the cylinder 1, opposite the first end, and provided with a through-hole 7 for sliding of the stem 3; seals 8 predisposed in the through-hole 7 of the second cap 6; and a coupling member 9 to which the stem 3 is fixed, the coupling member 9 having substantially a U-shape and comprising a base 11 and two lateral walls 12, 13, facing, which originate from the base 11. The piston 2 and the coupling member 9 are reciprocally conformed such that the coupling member 9 can embrace a part of the piston 2 and can perform limited oscillations with respect to the axis 2A of the piston 2. The coupling member 9 comprises two sliding wings 14, 15 which are fixed with respect to the free ends of the lateral walls 12, 13 of the coupling member 9 and which project such as to face the base 11 of the coupling member 9.

The base 11 of the coupling member 9 affords, for example, a small plate; the lateral walls 12, 13 of the coupling member 9 are for example perpendicular to the base 11, while the wings 14,15 are perpendicular to the lateral walls 12, 13 and are thus parallel to the base 11 (FIGS. 1, 2).

The piston 2 comprises: a first part 16 conformed such as to enable sealed sliding of the piston 2 along the internal walls 49 of the cylinder 1; a second part 17 rigidly fixed to the first part 16 and conformed such as to be embraced by the coupling member 9, and two gullies 18, 180, parallel and opposite, interposed between the first part 16 and the second part 17 of the piston 2 such as slidingly to receive the sliding wings 14, 15 of the coupling member 9.

In this way the coupling member 9 can slide along the gullies 18, 180 of the piston 2 when it embraces the second part 17 of the piston 2.

The volumetric doser 10 further comprises at least a blocking element 19, 20 of predetermined dimensions.

The coupling member 9 is provided with at least a through-hole 21, 22; the second part 17 of the piston 2 affords at least an opening 23, 24 at a relative wall 25 facing the coupling member 9 when the coupling member embraces the second part 17 of the piston 2; the through-hole 21, 22 and the opening 23, 24 are arranged in such a way that when the coupling member 9 embraces the second part 17 of the piston 2 the blocking element 19, 20 is insertable in the through-hole 21, 22 such as to at least partially occupy the opening 23, 24 and thus limit, by abutting against the lateral walls of the opening 23, 24, the possibility that the coupling member 9 can move with respect to the piston 2 when the coupling member 9 embraces the second part 17 of the piston 2.

The base 11 of the coupling member 9 exhibits an internal surface 31 which faces the wings 14 and an external surface 32, opposite the internal surface 31.

An undercut 33 can be made at the external surface 32 of the coupling member 9, for receiving an end of the stem 3; the stem 3 can be fixed to the coupling member 9, for example by welding. In the illustrated example of FIGS. 2A, 2B, the base 11 of the coupling member 9 is provided with two threaded through-holes 21, 22 arranged on opposite sides of the undercut 33; two blocking elements 19, 20 are comprised, which are in fact screws that engage in the threaded through-holes 21, 22. Also provided are two openings 23, 24 which are in fact niches.

The first part 16 of the piston is cylindrical, such as to enable, as specified, sealed sliding of the piston 2 along the internal walls 49 of the cylinder 1.

The second part 17 of the piston 2 comprises a bottom wall 25, for example flat, and a plurality of lateral walls. The lateral walls are formed by: two opposite walls 42, 43, for example flat and parallel, which respectively abut the lateral walls 12, 13 of the coupling member 9; two opposite walls 44, 45, which are not destined to abut any surface, having for example a hollow shape such as to form recesses; and four guide walls 46 each interposed between a corresponding flat lateral wall 42, 43 and a corresponding concave lateral wall 44, 45, which guide walls 46 are abreast with the internal walls 49 of the cylinder 1, for reasons which will become clear in the following part of the description. In other words, the guide walls have a cylindrical profile which is complementary to that of the internal walls 49 of the cylinder 1.

Figure 2B:
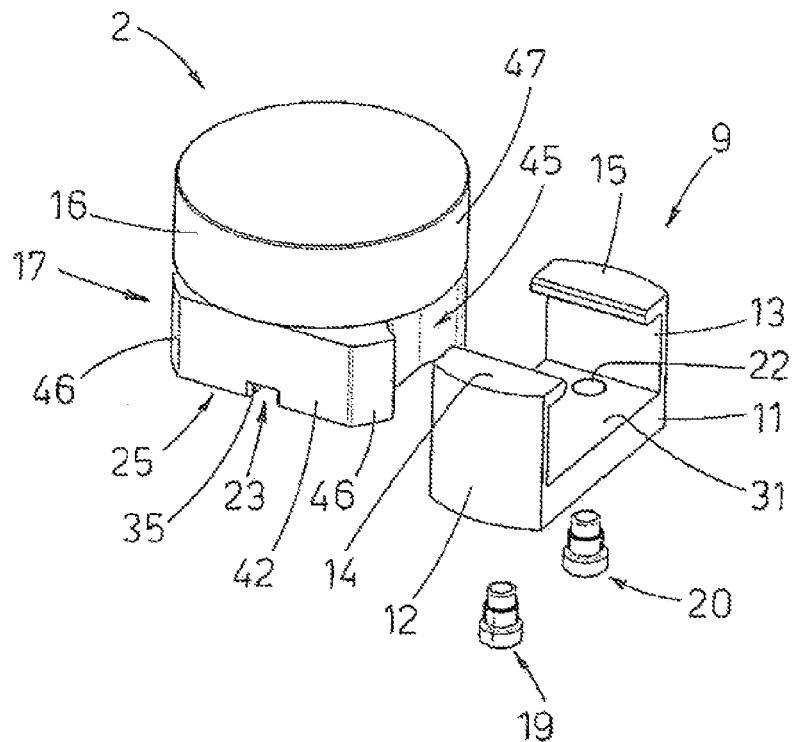
FIGS. 2A, 2B are two exploded perspective views of the piston and the coupling member of the volumetric batcher of FIG. 1.
Figure 2A:
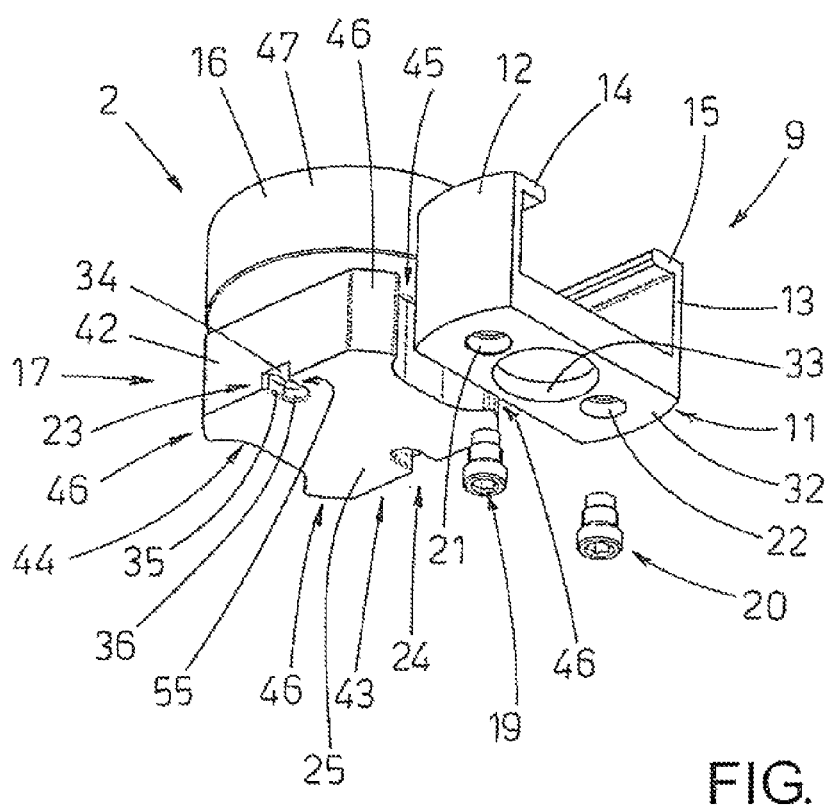

The openings 23, 24, are made at opposite edges of the bottom wall 25 of the second part 17 of the piston 2, such that for each opening 23, 24 apertures are provided both in the bottom wall 25 and in the corresponding lateral abutting walls 42, 43 (see FIGS. 2A, 2B). Each opening 23, 24 exhibits: two opposite lateral walls 35, 55, for example flat and parallel; a lateral wall 36 shaped as an arc of circumference and connected to the lateral walls 35, 55; and an upper wall 34 connected to the lateral walls 35, 55, 36.

The coupling member 9 is coupled to the piston 2 as follows: the coupling member 9 is inserted such that the relative wings 14, 15 slide along the gullies 18, 180 while the threaded through-holes 21, 22 are aligned with the openings 23, 24. This is made possible by the fact that the lateral walls 12, 13 of the coupling member 9 exhibit a reciprocal distance that is greater than the distance between the abutting walls 42, 43, enabling sliding of the coupling member 9 with respect to the second part 17 of the piston; in particular there is play between the lateral walls 12, 13 of the coupling member 9 and the abutting walls 42, 43 respectively facing them, and also play between the base 11 of the coupling member 9 and the opposite bottom wall 25 of the second part 17 of the piston 2 and between the sliding wings 14, 15 and the gullies 18, 180 of the piston 2; these degrees of play enable the coupling member 9 to oscillate with respect to the axis 2A of the piston 2, as will more fully emerge during the present description.

Thereafter the screws 19, 20 are applied, which are dimensioned such as not to contact the upper walls 34 of the openings 23, 24 when they engage in the threaded through-holes 21, 22; the screws 19, 20 project with respect to the internal surface 31 of the base 11 such that they can abut the lateral walls 35, 55, 36 of the openings 23, 24.

The portion of the screws 19, 20 projecting from the internal surface 31 of the base 11, i.e. the stalk, is smaller than the distance between the opposite lateral walls 35, 55 of the openings 23, 24, which enables a relative displacement of the coupling member 9 along the development direction of the gullies 18, 180, as the arrows of FIG. 4 demonstrate; FIG. 4 also shows two extreme positions assumed by the coupling member 9 with respect to the second part 17 of the piston 2, which correspond to the abutting of the screws 19, 20 against the opposite lateral walls 35, 55 of the openings 23, 24. References B1, B2 indicate the corresponding positions assumed by the axis of the coupling member 9, while reference C indicates the fixed position assumed by the piston 2 axis.

By effect of the play existing between the lateral walls 12, 13 of the coupling member 9 and the abutting walls 42, 43 of the second part 17 of the piston 2, the coupling member 9 can perform relative displacements in a perpendicular direction to the development direction of the gullies 18, 180 according to arrows K1, K2 indicated in FIGS. 5, 6.

The relative displacements in the perpendicular development direction of the gullies 18, 180 are limited by the screws 19, 20 touching against the lateral walls 36 of the openings 23, 24; in FIG. 5, reference B3 denotes the position assumed by the axis of the coupling member 9 when the screw 20 abuts the lateral wall 36 of the opening 24 (this abutting configuration is not visible in FIG. 5) by effect of a displacement of the coupling member 9 in direction K1; in FIG. 6 reference B4 denotes the position assumed by the axis of the coupling member 9 when the screw 19 abuts the lateral wall 36 of the opening 23 (this abutting configuration is visible in FIG. 6).

It follows that the coupling member 9 can have relative displacements in relation to the piston 2 on a plane that is perpendicular to the axis 2A of the piston itself; in particular, FIGS. 4, 5 and 6 show that the axis of the coupling member 9 can occupy positions internally of and on the perimeter of a circumference indicated by reference number 62 the centre of which C denotes the fixed position of the axis 2A of the piston 2.

Also when the coupling member 9 occupies relative positions with respect to the piston 2 such that a screw or both screws 19, 20 abut one or two corresponding lateral surfaces of the openings 23, 24, the lateral walls 12, 13 of the coupling member 9 do not contact the abutting walls 42, 43 of the second part 17 of the piston 2 by effect of the play as specified herein above, and this makes a relative inclination of the coupling member 9 possible with respect to the second part 17 of the piston 2. This enables the unit formed by the coupling member 9 or by the stem 3, when the stem 3 is fixed to the coupling member 9, to assume inclined positions with respect to the axis 2A of the piston 2; in general, this unit can perform limited oscillations with respect to the axis 2A of the piston 2, which simplifies the coupling operations of the actuator (not illustrated) with the stem 3 in order to move the piston 2. It can happen that the axis of the actuator does not become arranged such as to be concentric to the axis of the stem 2; the possibility of the coupling member 9—stem 3 unit to oscillate with respect to the axis 2A of the piston 2 enables a positioning of the axis 3A of the unit (in the illustrated example the coupling member 9 is conformed such that when it receives the stem 3 the relative axes are concentric, so reference can be made to a single common axis, referred to as 3A) concentric to the axis of the actuator, in such a way that no undesired transversal forces originate with respect to the axis of the stem 3. The force which the stem 3 transmits to the piston 2 via the actuator always has a parallel direction to the relative axis 3A of the stem 3, with a null transversal component, so that no undesired mechanical stresses are generated in the coupling between the coupling member 9 and the stem 3 and between the coupling member 9 and the piston 2.

During the normal functioning of the volumetric doser 10 for injection/expelling liquid or pasty substances into/from the cylinder 1, the piston 2 acts between a top dead centre, in which it is in the position of FIG. 1, and a bottom dead centre.

When the sterilization operations are performed, the piston 2 is moved towards the upper cap 4, thus passing beyond the top dead centre (this position is not illustrated in the figures); in the upper part of the cylinder 1, the walls 49 exhibit an increased diameter such as to enable passage of the sterilizing fluid also below the piston 2; in this configuration the walls 46 of the second part 17 of the piston 2 function as a guide for the piston 2.

The piston 2 is for example made of a ceramic material, while the coupling member 9 and the screws 19, 20 are made of stainless steel; thanks to the coupling realized between the coupling member 9 and the second part 17 of the piston 2, the relative effects consequent to the heat dilation, when the volumetric doser 10 is sterilized, are compensated for. This is thanks to the play as described above and to the possibility for the coupling member 9 to perform displacements on a perpendicular plane to the axis 2A of the piston 2 (reference is made to the circumference 62 illustrated in FIGS. 4, 5 and 6).

The different coefficients of heat dilation are therefore not the cause of any undesired stresses in the coupling between the piston 2 and the coupling member 9.

To minimize the effects connected to the heat dilation of the stainless steel screws 19, 20, they can be made with internal hollow parts; for example, the stem of the screws 19, 20 can be tubular.

The above has been described purely by way of non-limiting example, and any eventual constructional variants are considered to fall within the ambit of protection of the present technical solution, as claimed herein below.

The invention claimed is:

1. A volumetric doser (10) for batching liquid or pasty pharmaceutical substances, comprising:
   a cylinder (1);
   a piston (2), mobile along internal walls (49) of the cylinder (1) for displacing liquid or pasty pharmaceutical substances;
   a stem (3) exiting from the cylinder (1) for moving the piston (2);
   wherein:
   the volumetric doser (10) is provided with a coupling member (9) to which the stem (3) is fixable, the coupling member (9) having a substantially U-shaped form and comprising: a base (11) and two facing lateral walls (12, 13) which originate from the base (11);
   and wherein the piston (2) and the coupling member (9) are reciprocally conformed such that the coupling member (9) can embrace a part (17) of the piston (2) and can perform limited oscillations with respect to the piston (2) axis;
   wherein the coupling member (9) comprises two sliding wings (14, 15) which are respectively fixed to free ends of the lateral walls (12, 13) of the coupling member (9) itself and which project such as to face the base (11) of the coupling member (9);
   and wherein the piston (2) comprises: a first part (16) conformed such as to enable sealed sliding of the piston (2) along the internal walls (49) of the cylinder (1), a second part (17) rigidly fixed to the first part (16) and conformed such as to be embraced by the coupling member (9), and gullies (18, 180) interposed between the first part (16) and the second part (17) of the piston (2) such as slidingly to receive the sliding wings (14, 15) of the coupling member (9);
   the coupling member (9) being able to slide along the gullies (18, 180) of the piston (2) when it embraces the second part of the piston (2); and,
   further comprising at least a blocking element (19, 20), the coupling member (9) being provided with at least a through-hole (21, 22), the second part (17) of the piston (2) affording at least an opening (23, 24) in a relative wall (25) facing the coupling member (9) when the coupling member (9) embraces the second part (17) of the piston (2), the through-hole (21, 22) and the opening (23, 24) being arranged such that when the coupling member (9) embraces the second part (17) of the piston (2) the blocking element (19, 20) is insertable in the through-hole (21, 22) in order at least partially to occupy the opening (23, 24) and thus to limit the possibility that the coupling member (9) might move with respect to the piston (2) when the coupling member (9) embraces the second part (17) of the piston (2).

2. The volumetric doser (10) of claim 1, wherein the through-hole (21, 22) is afforded in the base (11) of the coupling member (9).

3. The volumetric doser (10) of claim 1, wherein the through-hole (21, 22) is threaded and in which the blocking element (19, 20) is a threaded element.

4. The volumetric doser (10) of claim 1, wherein the piston (2) is made of a ceramic material, while the coupling member (9) and the blocking element (19, 20) are made of stainless steel, and wherein the blocking element (19, 20) internally comprises hollow parts for compensating a consequent thermal dilation effect.

5. The volumetric doser (10) of claim 2, wherein the through-hole (21, 22) is threaded and in which the blocking element (19, 20) is a threaded element.

6. The volumetric doser (10) of claim 2, wherein the piston (2) is made of a ceramic material, while the coupling member (9) and the blocking element (19, 20) are made of stainless steel, and wherein the blocking element (19, 20) internally comprises hollow parts for compensating a consequent thermal dilation effect.

7. The volumetric doser (10) of claim 3, wherein the piston (2) is made of a ceramic material, while the coupling member (9) and the blocking element (19, 20) are made of stainless steel, and wherein the blocking element (19, 20) internally comprises hollow parts for compensating a consequent thermal dilation effect.

* * * * *